United States Patent
Palanichamy et al.

(10) Patent No.: US 6,924,379 B2
(45) Date of Patent: Aug. 2, 2005

(54) PROCESS FOR PREPARATION OF CYCLIC CARBONATE

(75) Inventors: Manikandan Palanichamy, Pune (IN); Sankar Meenakshisundaram, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 235 days.

(21) Appl. No.: 10/449,697

(22) Filed: May 30, 2003

(65) Prior Publication Data

US 2004/0242903 A1 Dec. 2, 2004

(51) Int. Cl.⁷ .............................................. C07D 317/12
(52) U.S. Cl. ..................................... 549/229; 549/228
(58) Field of Search ................................ 549/228, 229

(56) References Cited

U.S. PATENT DOCUMENTS

| | | | | |
|---|---|---|---|---|
| 4,331,604 A | * | 5/1982 | Renga et al. ................. | 549/230 |
| 4,892,954 A | * | 1/1990 | Brindopke et al. .......... | 549/229 |
| 5,153,333 A | * | 10/1992 | Schubert et al. ............ | 549/230 |
| 5,349,077 A | * | 9/1994 | Doya et al. .................. | 558/260 |
| 6,384,240 B1 | * | 5/2002 | Machac, et al. ............. | 549/230 |

* cited by examiner

*Primary Examiner*—Golam M M Shameem
(74) *Attorney, Agent, or Firm*—Ladas & Parry LLP

(57) ABSTRACT

A catalytic system comprising of Zinc-substituted polyoxometalate, $Na_{12}[WZn_3(H_2O)_2(ZnW_9O_{34})_2] \cdot 48H_2O$ and a Lewis base has been discovered to be efficient for chemical fixation of $CO_2$ with epoxides (I) to form cyclic carbonates of structure II as given below:

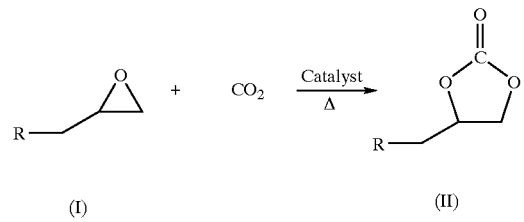

wherein R is selected from a halogen atom, aliphatic and aromatic group. The reaction was carried out at moderate $CO_2$ pressure of 60 psig and in the temperature range 100–140° C. with very high turn number of more than 40,000, with nearly a quantitative conversion and 95–99% selectivity. The Zinc-substituted polyoxometalate catalyst is easy to separate after the reaction by filtration and reusable for many cycles. The reaction can be carried out without any solvent.

11 Claims, No Drawings

PROCESS FOR PREPARATION OF CYCLIC CARBONATE

FIELD OF THE INVENTION

The present invention relates to a process for the preparation of cyclic carbonates. More particularly the present invention relates to the a process of cycloaddition of $CO_2$ to epoxide using catalytic system consists of Zinc-substituted-polyoxometalate catalyst and a Lewis base with very high turn over number. The present invention involves a new catalytic system comprising of Zinc-substituted polyoxometalate and a Lewis base such as dimethyl aminopyridine for production of cyclic carbonates from epoxides and carbon dioxide. More particularly, the present invention involves inexpensive catalyst system for the above said reaction with very high turn over number and also the catalyst can be reusable.

BACKGROUND OF THE INVENTION

Carbon dioxode is inexpensive, highly abundant and can be used as a $C_1$ feed stock for the synthesis of cyclic carbonates, polycarbonates etc. These transformations are attractive processes from the view of point "green chemistry" because $CO_2$, a global warming gas, can be incorporated without any side product and also it is a renewable $C_1$ source. Organic cyclic carbonates have been widely used as monomers, aprotic organic solvents, pharmaceutical/fine chemical intermediates, electrolytic components, chemical intermediates etc. and are also useful in many biomedical applications. Cyclic carbonates are also used to synthesis dialkyl carbonates which are of industrial importance for many potential applications.

Several catalytic materials including amines, phosphines, metal oxides have been reported in the recent years for the synthesis of cyclic carbonates from $CO_2$. Transition metal ion based catalysts in conjunction with a Lewis base have been reported to be efficient for the $CO_2$ fixation reaction. A substantial number of patents and articles are available in the literature which describe production of alkylene carbonates from alkylene oxides and carbon dioxide. For example, Japanese Patent JP 47-31981 discloses synthesis of alkylene carbonates from an epoxide and carbon dioxide in the presence of a Lewis acid (e.g $ZnCl_2$, $AlCl_3$ etc) and an organic base. The process was carried out at 100–400° C. and 19.6–294 bar $CO_2$ pressure with 90% yield. Japanese Patent JP 51-13,720 discloses similar catalyst system where the temperature was 80–130° C. and pressure was less than 70.9 bar with approximately 90% yield. Chinese patent, CN1343668A by Deng et al teaches a process for synthesizing cyclic carbonate by a catalyst composed of azacyclic compound, non-metal halide and alkali metal halide or ammonium tetrabutyl bromide at temperature 100–140° C. and 1.5–4.5 MPa pressure.

U.S. Pat. No. 2003/0023109A1 by Schlosberg et al and WO 03/000641 A1 by Buchanan et al describe integrated process for preparation of dialkyl carabonates where the first step involves synthesis of cyclic carbonates using halogen free alkyl ammonium salt catalysts at temperature 100–200° C. and $CO_2$ pressure up to 1000 psig. U.S. Pat. No. 2,773,070 by Lichtenwalter et al discloses reaction of alkylene oxides with carbon dioxide in the presence of certain class of ammonium halides where the process was operated at 100–225° C. and pressure of more than 300 psig. U.S. Pat. No. 2,873,282 by McCellan at al used catalyst comprised of hydroxide, carbonate or bicarbonates of quaternary ammonium compounds and the process operates at 1000–1500 psig and at 150–175° C. U.S. Pat. No. 5,153,333 by Schubert et al discloses a process of preparing 2-oxo-1,3-dioxolanes comprises of reacting an epoxy compound with carbon dioxide at 60–200° C. at normal pressure in the presence of a quaternary phosphonium compound as catalyst. Japanese patent JP1975000077840 describes preparation of cyclic carbonates from epoxide and $CO_2$ in good yield using a Grignard reagent and a N-containing compound. Russian patent RU2128658C1 by Dobyleva et al discloses a method of preparation of cyclic carbonates with a cobalt halide catalyst at temperature 130–150° C. and pressure of 1–1.5 MPa.

Though good conversion and selectivity have been achieved as reported in the literature, most of the reported catalytic systems carry at least one of the following disadvantages: (1) need for high concentration of catalyst, (2) instability of catalyst, (3) air-sensitivity, (4) need for co-solvent, (5) requirement of higher temperature/pressure, (6) difficulty in separating the catalyst after the reaction for reuse etc. So efficient catalyst composite operating at milder experimental conditions preferably without need for any organic solvents but with very high turn over number is of great interest.

OBJECTS OF THE INVENTION

The main object of the present invention is to provide an improved process for the preparation of cyclic carbonates which obviates the drawbacks as detailed above.

Another object of the present invention is to carry out above reaction under milder experimental conditions with short duration time and without any solvent.

SUMMARY OF THE INVENTION

Accordingly the present invention provides a process for preparing a cyclic carbonate of formula (II) comprising reacting an epoxide of formula (I) over a catalytic system consisting of a zinc-substituted polyoxometalate and a Lewis base at a temperature in the range of 100–150° C. and at 60 to 150 psig pressure of $CO_2$, bringing the reaction mixture to room temperature and atmospheric pressure, separating the catalyst to obtain the desired carbonate wherein R is selected from a halogen atom, aliphatic and aromatic group

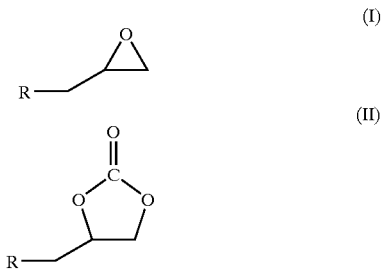

In one embodiment of the invention, the Lewis base is selected from the group consisting of dimethyl aminopyridine, methylated imidazolse and trialkyl amine.

In another embodiment of the present invention, the catalytic system comprises Zinc-substituted polyoxometalate catalyst of formula, $Na_{12}[WZn_3(H_2O)_2(ZnW_9O_{34})_2] \cdot 46H_2O$ and a Lewis base such as dimethyl aminopyridine.

In another embodiment of the invention, the reaction is carried out in the presence of an inert solvent selected from the group consisting of a halogenated alkane, benzene and an alkylated benzene.

In a further embodiment of the invention, the halogenated alkane is selected from the group consisting of dichloromethane and 1,2-dichloroethane.

In another embodiment of the invention, the alkylated benzene comprises toluene.

In another embodiment of the invention, the ratio of Zinc-substituted polyoxometalates and Lewis base is in the range of 1:1 to 1:4 and preferably 1:3.

In yet another embodiment, the mole ratio of concentration of catalyst system and the epoxide is in the range of 1:10000 to 1:50000.

In yet another embodiment, the carbon dioxide pressure is in the range 60 to 150 psig without altering the reaction time, conversion or selectivity.

In yet another embodiment, the Zinc-substituted polyoxometalate catalyst is separable and reusable.

DETAILED DESCRIPTION OF THE INVENTION

A catalytic system consisting of Zinc-substituted polyoxometalate, $Na_{12}[WZn_3(H_2O)_2(ZnW_9O_{34})_2] \cdot 48H_2O$ and a Lewis base has been found to be efficient for chemical fixation of $CO_2$ with epoxides (I) to form cyclic carbonates of structure (II):

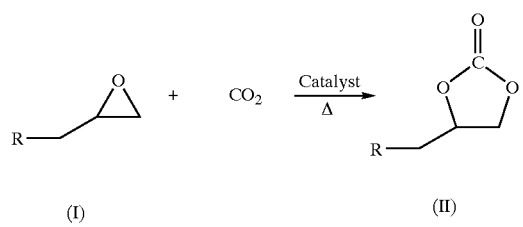

wherein R is halogen atom, aliphatic or aromatic groups. The reaction was carried out at moderate $CO_2$ pressure of 60 psig and in the temperature range 100–140° C. with very high turn number of more than 40,000, with nearly a quantitative conversion and 95–99% selectivity. The Zinc-substituted polyoxometalate catalyst is easy to separate after the reaction by filtration and reusable for many cycles. The reaction can be carried out without any solvent.

In a feature of the present invention, the process of invention can be carried out with short reaction time of three hours especially at temperatures 140° C. with high conversion and selectivity and with very high turn over numbers. In another feature of the present invention, only very small amount of catalyst is required.

The Zinc-substituted polyoxometalates are prepared by the process described Tourné, C. M.; Tourné, G. F.; Zonnevijlle, F. *J Chem. Soc. Dalton Trans*, 1991, 143–155.

Process of the present invention is described herein below with reference to illustrative examples and should not be considered to limit the scope of present invention in any manner.

EXAMPLE 1

This is an example of preparation in which a solution of $Na_2WO_4 \cdot 2H_2O$ (127 g, 0.38 mol) in water (350 cm³) heated at 80–85° C. and vigorously stirred, treated with 14 mol dm$^{-3}$ nitric acid (25 cm³, 0.35 mol) until the precipitate formed dissolved entirely, then, a solution of zinc nitrate hexahydrate (29.8 g, 0.10 mol) in water (100 cm³) was added with continuous stirring and heating at 90–95° C. The solution is filtered and recrystallized from water.

EXAMPLE 2

This is an example of a typical reaction in which a stainless steel autoclave equipped with over head stirrer and gas inlet, outlet pipes and pressure gauge charged with 0.0027 mmol of Zinc-substituted polyoxometalate, 3 moles equivalent dimethyl aminopyrdine, hexadecane (internal standard for GC analysis), different mmol equivalents of epichlrohydrine (epoxide) as given in Table (1) herein below and 10 ml of $CH_2Cl_2$. After purging with $CO_2$, the reaction mixture was pressurized to 60 psig and heated to temperature 100° C. The overhead stirring speed was around 400 rpm. The course of the reaction was monitored by taking samples repeatedly, and determining the residual content as well as the cyclic carbonate formation by GC, IR, NMR and GC-MS. The reaction is completed at 24 hrs at this temperature except for the 135 mmol equivalent epoxide reaction where the completion of reaction needed nearly 29 hrs. During the entire course of the reaction selectivity remains more than 95%. Quantification of the product by mass balance yield is always 2–5% less than calculated from GC and NMR, preferably due to loss during handling and part of the product sticking to the wall of the autoclave.

TABLE (1)

| S. No. | Catalyst, mmol | Epoxide, mmol | Time, hrs | Conversion, mol % | Selectivity, mol % |
|---|---|---|---|---|---|
| 1 | 0.0027 | 10.8 | 24 | 99.0 | 95.0 |
| 2 | 0.0027 | 16.2 | 24 | 99.0 | 97.2 |
| 3 | 0.0027 | 27.0 | 24 | 99.0 | 97.4 |
| 5 | 0.0027 | 135.0 | 29 | 99.0 | 96.9 |

EXAMPLE 3

This is an example of a typical reaction in which a stainless steel autoclave equipped with over head stirrer and gas inlet, outlet pipes and pressure gauge charged with 0.0027 mmol of Zinc-substituted polyoxometalate catalyst, 3 moles equivalent dimethyl aminopyridine, hexadecane (internal standard for GC analysis), 27 mmol equivalent of epichlorohydrine (epoxide) and 10 ml of $CH_2Cl_2$. After purging with $CO_2$, the reaction mixture was pressurized to 60 psig and heated to different temperature range 100–150° C. and the results are as given in Table (2) herein below. The course of the reaction was monitored by repeatedly taking samples and determining the residual content as well as the cyclic carbonate formation by GC, IR, NMR and GC-MS. The time required for complete epoxide conversion decreases with increasing temperature.

TABLE (2)

| S. No. | Catalyst, mmol | Epoxide, mmol | Temp, ° C. | Time, hrs | Conversion, mol % | Selectivity, mol % |
|---|---|---|---|---|---|---|
| 1 | 0.0027 | 27.0 | 100 | 24 | 99 | 97.8 |
| 2 | 0.0027 | 27.0 | 120 | 8 | 99 | 96.5 |
| 3 | 0.0027 | 27.0 | 140 | 3 | 99 | 96.0 |
| 4 | 0.0027 | 27.0 | 150 | 2 | 99 | 93.5 |

EXAMPLE 4

This is an example of a typical reaction in which a stainless steel autoclave equipped with over head stirrer and gas inlet, outlet pipes and pressure gauge charged with 0.0027 mmol of Zinc-substituted polyoxometalate catalyst, 3 moles equivalent dimethylamino pyridine, hexadecane (internal standard for GC analysis), 27 mmol equivalent of epichlorohydrine (epoxide) and 10 ml of $CH_2Cl_2$. After purging with $CO_2$, the reaction mixture was pressurized to different pressure range 60–150 psig and heated to 140° C. It was discovered that conversion and selectivity are independent of carbon dioxide pressure in the range 60–150 psig.

EXAMPLE 5

This is an example to check the role of the Zinc-substituted polyoxometalate catalyst and the Lewis base, wherein the experiments are carried out in a stainless steel autoclave equipped with over head stirrer and gas inlet, outlet pipes and pressure gauge. Three experiments are carried out: (i) in the absence of Zinc-substituted polyoxometalate, (ii) in the absence of Lewis base and (iii) in the absence of both Zinc-substituted polyoxometalate and the Lewis base, and the results are given in Table (3) herein below. It is observed that both experiments (i) and (ii) proceeded only up to 49 and 65% conversion respectively. The partial conversion probably indicates their roles in the activation of $CO_2$ and epoxide. In the absence of both Zinc-substituted polyoxometalate catalyst and dimethyl aminopyridine, the conversion is very low. However, the coexistence of Zinc-substituted polyoxometalate catalyst and the base seems to be important for the high activity in promoting the cycloaddition reactions.

TABLE (3)

| Entry No. | Zn-POM Equivalent | DMAP equivalents | Conversion (mol %) | Selectivity (mol %) | TON[a] |
|---|---|---|---|---|---|
| 1 | 1 | 3 | 97.0 | 98.0 | 9,504 |
| 2 | 1 | 0 | 49.2 | 91.3 | 4,491 |
| 3 | 0 | 3 | 65.0 | 98.0 | — |
| 4 | 0 | 0 | 7.9 | 69.0 | — |

Reaction Conditions: temperature: 140° C., $pCO_2$:60 psig, $CH_2Cl_2$:10 ml; Epoxide: 2.499 g, catalyst: 0.016 g, time: 3 hrs. [a]:TON, moles of cyclic carbonates produced per mole of zinc-substituted polyoxometalate catalyst. DMAP: Dimethylamino pyridine, Zn-POM: Zinc-substituted polyoxometalate

EXAMPLE 6

This is an example of a typical reaction in which a stainless steel autoclave equipped with over head stirrer and gas inlet, outlet pipes and pressure gauge charged with 0.0027 mmol of zinc-substituted polyoxometalate catalyst, 3 moles equivalent dimethylamino pyridine, hexadecane (internal standard for GC analysis), 27 mmol equivalents of epichlorohydrin (epoxide) and with 10 ml of organic solvents like dichloromethane and another experiment without any organic solvents. After purging with $CO_2$, the reaction mixture was pressurized to 60 psig and heated to temperature 100° C. The overhead stirring speed was around 400 rpm. The course of the reaction was monitored by repeatedly taking samples and determining the residual content as well as the cyclic carbonate formation by GC, IR, NMR and GC-MS and we found that no impact of the presence of solvent.

EXAMPLE 7

This is an example to find out the maximum turn over number for the present catalytic system. In the typical reaction a stainless steel autoclave equipped with over head stirrer and gas inlet, outlet pipes and pressure gauge charged with different epichlorohydrine/catalyst-system mole ratio and dimethylamino pyridine of 3 moles equivalent of catalyst concentration, hexadecane (internal standard for GC analysis) and 10 ml of dichloromethane, at 60 psig $CO_2$ pressure, heated to 140° C. The course of the reaction was monitored by repeatedly taking samples and determining the residual content as well as the cyclic carbonate formation by GC, IR, NMR and GC-MS and the results at the end of three hours are given in Table (4) herein below.

TABLE (4)

| Entry No. | Epichlorohydrine (epoxide) | DMAP equiv. | Conversion (%) | Selectivity (%) | TON[a] |
|---|---|---|---|---|---|
| 1 | 2.499 g | 3 | 97.0 | 98.0 | 9,504 |
| 2 | 6.244 g | 3 | 97.8 | 98.2 | 24,009 |
| 3 | 12.488 g | 3 | 83.5 | 98.2 | 40,998 |

[a]TON, moles of cyclic carbonates produced per mole of zinc-substituted polyoxometalate catalyst

EXAMPLE 7

This is an example to test the reusability of the Zinc-substituted polyoxometalate after the first reaction is completed. After the completion of the reaction, the reaction mixture was centrifuged and the Zinc-substituted polyoxometalate was separated by filtration and was tested with fresh addition of dimethylamino pyridine base for a new reaction in which a stainless steel autoclave equipped with over head stirrer and gas inlet, outlet pipes and pressure gauge charged with epoxide/recovered-catalyst mole ratio 10,000 dimethylamino pyridine of 3 moles equivalent of catalyst concentration, hexadecane (internal standard for GC analysis) and 10 ml of dichloromethane, at 60 psig $CO_2$ pressure, heated to 140° C. The course of the reaction was monitored by repeatedly taking samples and determining the residual content as well as the cyclic carbonate formation by GC, IR, NMR and GC-MS and the results at the end of three hours are given in Table (5) herein below. The selectivity and conversion were as good as the fresh reaction. Such a cycle is repeated thrice and found that the conversion is bit low only after second use though the selectivity remains very high (more than 98%).

TABLE (5)

| Entry No. | Zn-POM | DMAP equiv. | Conversion (mol %) | Selectivity (mol %) | TON[a] |
|---|---|---|---|---|---|
| 1 | I Reuse | 3 | 98.6 | 97.8 | 9,643 |
| 2 | II Reuse | 3 | 94.5 | 98.1 | 9,270 |
| 3 | III Reuse | 3 | 80.2 | 98.0 | 7,859 |

[a]TON, moles of cyclic carbonates produced per mole of zinc-substituted polyoxometalate catalyst.

EXAMPLE 8

This is an example to test the potential of the present catalyst system for other epoxides. Epoxides such as epichlorohydrin, styrene oxide, 1,2 epoxy butane were used for the experiment in which a stainless steel autoclave equipped with over head stirrer and gas inlet, outlet pipes and pressure gauge charged with epoxide/catalyst mole ratio 10,000 dimethylamino pyridine of 3 moles equivalent of catalyst concentration, hexadecane (internal standard for GC analysis) and 10 ml of dichloromethane, at 60 psig $CO_2$ pressure, heated to 140° C. and found all are active for cycloaddition of $CO_2$ reaction.

The main advantages of the present invention are:
1. Only small amount of catalyst is needed for the completion of reaction and as low as epoxide/catalyst system mole ratio ~40000 is sufficient with very high selectivity. Thus the present catalyst system offers high turn over numbers.
2. The catalyst component, $Na_{12}[WZn_3(H_2O)_2(ZnW_9O_{34})_2]\cdot 46H_2O$ is easy to prepare and inexpensive.
3. The catalyst component, $Na_{12}[WZn_3(H_2O)_2(ZnW_9O_{34})_2]\cdot 46H_2O$ is not air-sensitive and stable throughout the reaction.
4. The catalyst component, $Na_{12}[WZn_3(H_2O)_2(ZnW_9O_{34})_2]\cdot 46H_2O$ can be separated after the reaction and can be reused for many reaction cycles.
5. The present catalyst system does not need any organic solvent for the reaction.
6. With the present catalyst systems, the $CO_2$ fixation reaction can be carried out under milder reaction conditions.

We claim:

1. A process for preparing a cyclic carbonate of formula (II) comprising reacting an epoxide of formula (I) over a catalytic system consisting of a zinc-substituted polyoxometalate and a Lewis base at a temperature in the range of 100–150° C. and at 60 to 150 psig pressure of $CO_2$, bringing the reaction mixture to room temperature and atmospheric pressure, separating the catalyst to obtain the desired carbonate

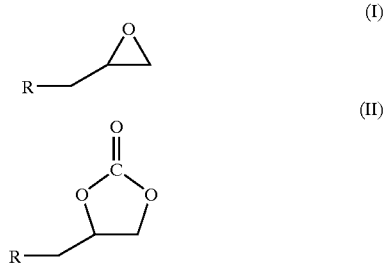

wherein R is selected from a halogen atom, aliphatic and aromatic group.

2. A process as claimed in claim 1 wherein the Lewis base is selected from the group consisting of dimethyl aminopyridine, methylated imidazolse and trialkyl amine.

3. A process as claimed in claim 1 wherein the catalytic system comprises Zinc-substituted polyoxometalate catalyst of formula, $Na_{12}[WZn_3(H_2O)_2(ZnW_9O_{34})_2]\cdot 46H_2O$ and a Lewis base such as dimethyl aminopyridine.

4. A process as claimed in claim 1 wherein the reaction is carried out in the presence of an inert solvent selected from the group consisting of a halogenated alkane, benzene and an alkylated benzene.

5. A process as claimed in claim 4 wherein the halogenated alkane is selected from the group consisting of dichloromethane and 1,2-dichloroethane.

6. A process as claimed in claim 4 wherein the alkylated benzene comprises toluene.

7. A process as claimed in claim 1 wherein the ratio of Zinc-substituted polyoxometalates and Lewis base is in the range of 1:1 to 1:4.

8. A process as claimed in claim 7 wherein the ratio of Zinc-substituted polyoxometalates and Lewis base 1:3.

9. A process as claimed in claim 1 wherein the mole ratio of concentration of catalyst system and the epoxide is in the range of 1:10000 to 1:50000.

10. A process as claimed in claim 1 wherein the reaction time, conversion or selectivity are independent of carbon dioxide pressure.

11. A process as claimed in claim 1 wherein the Zinc-substituted polyoxometalate catalyst is separable and reusable.

* * * * *